United States Patent [19]

Xu et al.

[11] Patent Number: 5,761,336

[45] Date of Patent: Jun. 2, 1998

[54] APERTURE OPTIMIZATION METHOD PROVIDING IMPROVED DEFECT DETECTION AND CHARACTERIZATION

[75] Inventors: James J. Xu, Sunnyvale; John E. Fertig, Ben Lomond; Ken K. Lee, Los Altos, all of Calif.

[73] Assignee: Ultrapointe Corporation, San Jose, Calif.

[21] Appl. No.: 586,061

[22] Filed: Jan. 16, 1996

[51] Int. Cl.[6] .......................... G07B 21/00; G01R 31/26
[52] U.S. Cl. ........................................... 382/141; 356/237
[58] Field of Search ................................. 382/141, 144, 382/145, 148, 149; 348/87, 126; 356/237; 364/468.17; 437/8

[56] References Cited

U.S. PATENT DOCUMENTS

| | | | |
|---|---|---|---|
| 4,377,340 | 3/1983 | Green et al. | 356/237 |
| 4,871,257 | 10/1989 | Suzuki et al. | 356/400 |
| 4,952,058 | 8/1990 | Noguchi et al. | 356/237 |
| 5,338,630 | 8/1994 | Yoon et al. | 430/30 |
| 5,602,645 | 2/1997 | Tabata et al. | 356/394 |

OTHER PUBLICATIONS

"Integration of Automated Defect Classification Into Integrated Circuit Manufacturing", Louis Breaux, James Kawski and Baljit Singh, *IEEE/SEMI Advanced Semiconductor Manufacturing Conference*, 1994.

"Techniques for Syntactic Analysis of Images with Application for Automatic Visual Inspection", Youling Lin, M.S., *A Dissertation in Business Administration*, Dec. 1990.

*Primary Examiner*—David K. Moore
*Assistant Examiner*—Brian P. Werner
*Attorney, Agent, or Firm*—Skjerven, Morrill, MacPherson, Franklin & Friel LLP; Arthur J. Behiel

[57] ABSTRACT

Disclosed is method of adjusting a microscope aperture to obtain the highest possible defect detection rate for a particular type of target. According to the method, an operator obtains an image of a calibration target and visually analyzes the image for defects. The operator then uses a defect detection process to analyze the image to obtain another set of defect information. This second set of defect information is compared with the visually obtained defect information to determine the accuracy of the defect detection performed by the defect detection process; a perfect match indicates 100% accurate defect detection. The operator then changes the aperture diameter and repeats the process to obtain a second set of defect information. This second set of defect information is, like the first set, compared with the visually obtained defect information. This process is repeated as many times as are necessary to determine which aperture diameter results in the highest defect detection rate.

16 Claims, 3 Drawing Sheets

5,761,336

APERTURE OPTIMIZATION METHOD PROVIDING IMPROVED DEFECT DETECTION AND CHARACTERIZATION

CROSS-REFERENCES TO RELATED APPLICATIONS

The present application is related to the following commonly owned, co-pending U.S. patent applications:

1. "A Method and Apparatus for Performing an Automatic Focus Operation," by Timothy V. Thompson, Christopher R. Fairley, and Ken K. Lee, application Ser. No. 08/183,536, filed on Jan. 18, 1994;
2. "A Method and Apparatus for Automatic Focusing of a Confocal Laser Microscope," by Christopher R. Fairley, Timothy V. Thompson, and Ken K. Lee, application Ser. No. 08/373,145, filed on Jan. 17, 1995;
3. "Automated Surface Acquisition For a Confocal Microscope," by Ken K. Lee, application Ser. No. 08/483,234, filed on Jun. 7, 1995;
4. "Method for Characterizing Defects on Semiconductors," by Ken K. Lee and Bruce W. Worster, application Ser. No. 08/497,162, filed Jun. 30, 1995; and
5. "Laser Imaging System For Inspection and Analysis of Sub-Micron Particles," by Bruce W. Worster, Dale E. Crane, Hans J. Hansen, Christopher R. Fairley, and Ken K. Lee, application Ser. No. 08/518,284 filed on Dec. 7, 1995.

These applications are incorporated herein by this reference.

BACKGROUND

Defects in the form of structural flaws, process residues, and external contamination occur during the production of semiconductor wafers. Defects are typically detected by a class of instruments called defect scanners. Such instruments automatically scan wafer surfaces and detect optical anomalies using a variety of techniques. The locations of these anomalies with respect to the pattern of semiconductor devices on the wafer surface are recorded. This information, or "defect map," is stored in a computer file and sent to a defect review station.

Using the defect map to locate each defect, a human operator observes each defect under a microscope and characterizes each defect according to type (e.g., particle, pit, scratch, or contaminant). Information gained from this process is used to correct the source of defects, and thereby improve the efficiency and yield of the semiconductor production process. Unfortunately, people are relatively slow and are quickly fatigued by the highly repetitive tasks of observing and characterizing defects.

Methods of automatically characterizing defects, collectively known as "Automatic Defect Characterization," or "ADC," have been developed to overcome the disadvantages of manual defect characterization. Conventional microscope-based review stations are automated to load a wafer that has been mapped for defect location by a defect scanner. Once the mapped wafer is loaded, the review station:

1. positions the wafer, using the defect map, to image the site of a defect;
2. focuses on the site of the defect;
3. captures a digital image of the site using a digital TV camera;
4. processes and analyzes the captured image of the site to locate the defect; and
5. further analyzes the data to characterize the defect.

The above process is repeated for each defect (or a predetermined subset of defects) on the wafer. The wafer is then unloaded and the process is repeated for another wafer. By eliminating a fatiguing and highly repetitive task, such automated review stations reduce labor costs and provide improved consistency and accuracy over human operators.

Conventional ADC systems capture a conventional white-light microscope image as an array A representing a two-dimensional image. The image is an x-y array of n by m pixels, where typical values might be n=640, m=480, or n=512, m=512. This array A may be represented as:

$$A(x, y, Ir, Ig, Ib)$$

where x and y are pixel coordinates, and Ir, Ig, and Ib represent the intensities of the red, green, and blue image components, respectively. Of course, grey scale images may also be used, as may other color schemes, such as those of the YUV and YIQ commercial standard video formats. In the case of a gray scale image, a single intensity parameter Ig is used.

In addition to imaging the defect site, at least one reference image $A_{ref}$ is also stored. The reference image may be a previously stored data-base image of a known-good area of the same or a similar die on the same or on a similar wafer, or it may be a specific image taken from e.g. an adjacent die. The reference image is compared with the image containing the defect. Differences between the two images indicate the location and extent of the defect.

Multiple reference images are usually required because slight differences in focus position between the reference and test images may cause false discrepancies to appear. In some cases, a separate reference image is not taken, and instead the reference image is a portion of the same image containing the defect, but from a region of the image where no defect occurs. In general, this latter method is faster but less reliable than methods that use a separate reference image, and works only for images containing repetitive structures or patterns.

Several conventional techniques are available to process images for automatic defect characterization. One such technique is described in the copending application entitled "Method for Characterizing Defects on Semiconductors," which has been incorporated by reference. For further discussion of conventional ADC techniques, see the IBM technical disclosure entitled "Automated Classification of Defects in Integrated Circuit Manufacturing," by Frederick Y. Wu, et al., which is incorporated herein by this reference.

Though automatic defect characterization has been shown to be very valuable, conventional systems are far from perfect. Comparisons between test and reference images are often flawed by e.g. electronic noise, misalignment, or improper focus of one or both images. Consequently, defects are often either missed or falsely detected. Therefore, what is needed is a more accurate method of automatically detecting and characterizing defects.

SUMMARY

The present invention addresses the aforementioned need to improve defect detection and characterization by optimizing image resolution for different types of targets. We were surprised to discover that the optimized image resolution for defect characterization is not necessarily the highest resolution, and is different for different types of targets. We have taken advantage of our discovery by inventing a method of determining the optimized image resolution for detecting and characterizing defects on various types of targets.

According to our method, a microscope operator provides a calibration sample of a particular target type and visually analyzes the sample for defects to obtain calibration data. The operator then uses the microscope to obtain a second image of the calibration sample with the aperture set to some known diameter and the illumination intensity set to some known value.

Next, the second image is compared with an image of a reference surface, such as a defect-free adjacent area on the same sample target. The comparison results in a set of difference data that represents the differences between the second image and the defect-free reference image. Because the second image, if free of defects, would ideally be precisely the same as the reference image, differences between the two images are interpreted to be defects of the second image. Thus, the difference data, a type of "defect information," is used to determine e.g. the location, outline, and size of defects.

The next step involves adjusting the intensity of the light source up and down. At each setting, the location, outline, and size of detected defects are recorded and visually compared with the reference image. A number of the detected "defects" are typically not true defects, but are instead artifacts of e.g. misalignment or focus differences between the target and the reference surface, electronic noise, and normal process variations between the target and the reference surface. The intensity setting providing the highest ratio of true defects to false defects is recorded.

The operator then changes the diameter of the aperture and the light intensity, thereby changing the image resolution and the depth of focus of the microscope, and obtains a third image of the calibration sample to obtain a second set of difference data, or "defect information." The second set of difference data is then compared with the first set. The operator may then choose the aperture diameter and light intensity that resulted in the most accurate defect detection, or may repeat the process any number of times to empirically define the aperture diameter/light intensity combination that results in the highest defect-detection accuracy.

Thus, in accordance with our inventive method, a microscope operator may use the accuracy of defect detection as the feedback for determining the optimal image resolution to achieve the most accurate defect detection for a given target type.

DETAILED DESCRIPTION

Figure 1:
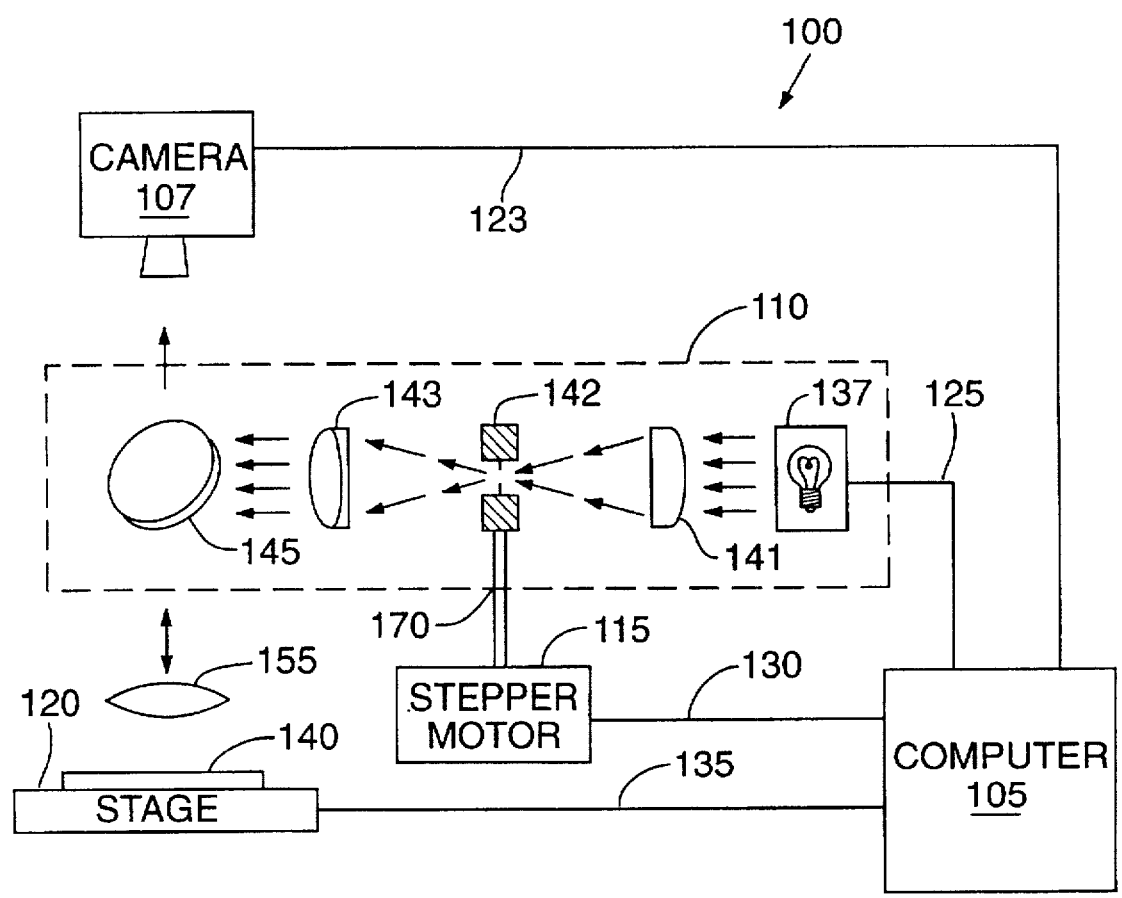
FIG. 1 is a schematic diagram of an imaging system 100 according to the present invention.

FIG. 1 is a schematic diagram of an imaging system 100 according to the present invention. Imaging system 100 includes a computer 105 connected to a video camera 107, an illuminator 110, a stepper motor 115, and a stage 120 via buses 123, 125, 130, and 135, respectively. Illuminator 110 includes a light source 137 that shines light toward e.g. a target wafer 140 through a collection lens 141, an aperture body 142, a collimator lens 143, a beam splitter 145, and an objective lens 155. The light then reflects off the surface of target wafer 140 back through objective lens 155 and beam splitter 145. This reflected light conveys an image of target wafer 140 to camera 107, which digitizes the image. Camera 107 transmits the digitized image to a monitor (not shown), allowing the imaging to be accomplished without the use of microscope eyepieces.

Imaging system 100 is a modified version of the white-light imaging system used in the Ultrapointe Laser Imaging System available from Ultrapointe Corporation of San Jose, Calif. The modification of imaging system 100 is described below in connection with FIGS. 2-3B. Version 2 of the user's manual for the Ultrapointe Laser Imaging System, which was published in 1995, is incorporated herein by this reference. A microscope illuminator for use with the invention is available from Olympus of Japan as part no. 5LM220.

Computer 105 is e.g. a high-speed RISC graphical workstation, such as a Silicon Graphics Indy™ manufactured by Silicon Graphics of Mountain View, Calif., or equivalent, capable of handling concurrent tasks of robot functions, stage motion, operator interface, and optics control, while also performing image processing functions and ADC. In addition, computer 105 has a windowing user interface and high-resolution color graphics.

Aperture body 142 is connected to stepper motor 115 by a mechanical lever 170 that, when driven by stepper motor 115, affects the diameter of the aperture (i.e., changes the diameter of the hole in the center of aperture body 142). Stepper motor 115 is coupled to computer 105 so that the operator can, by entering a number of stepper-motor counts into computer 105, select an appropriate aperture diameter. In one embodiment, stepper motor 115 is a linear stepper motor manufactured by Haydon Switch and Instrument of Waterbury, Conn., as part no. 26844-12. That stepper motor is capable of moving lever 170 over the travel range of lever 170 in four-thousandths-of-an-inch (0.004") stepper-motor counts.

Figure 2:
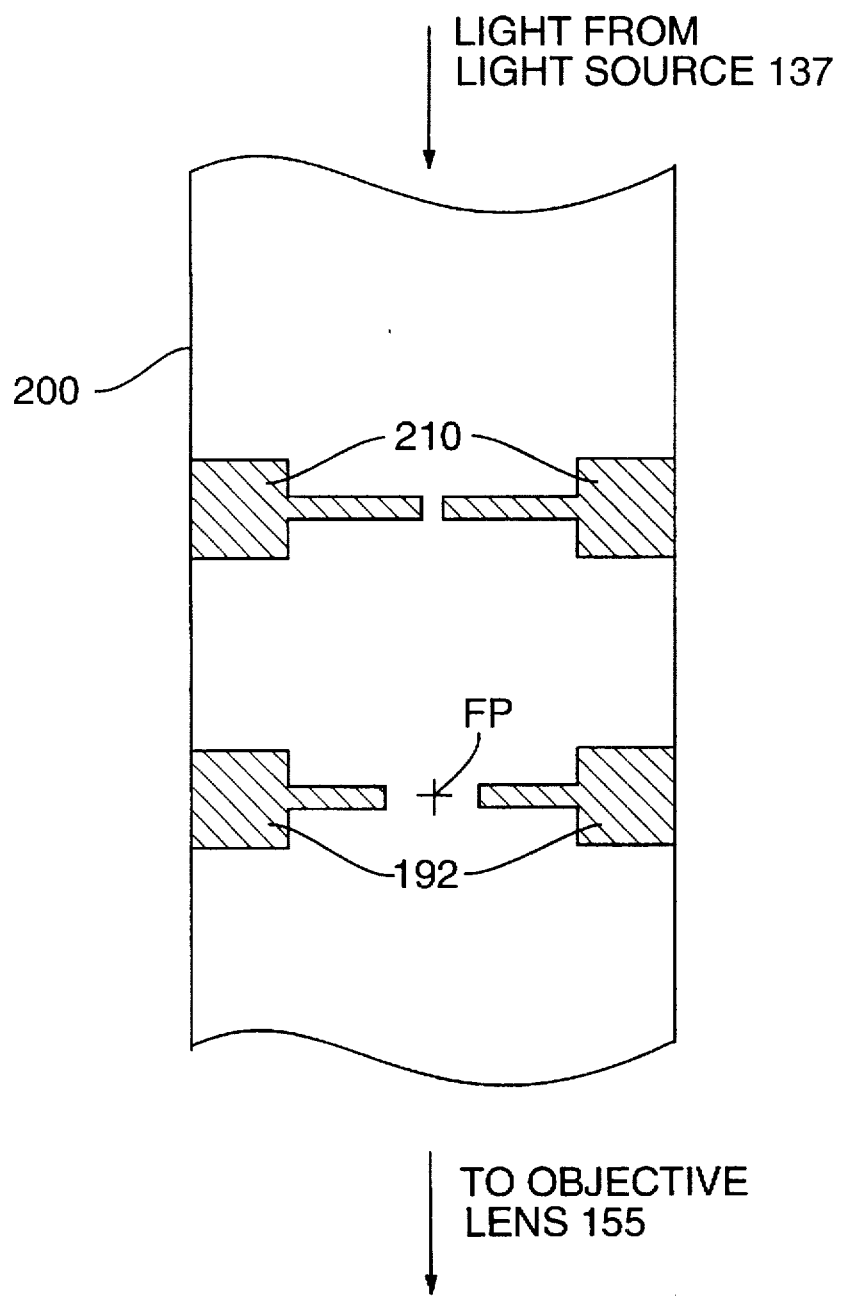
FIG. 2 shows a section of an illuminator body 200 that supports aperture body 142 and a pin hole 210 in a conventional microscope.

FIG. 2 shows a section of a prior-art illuminator body 200 that supports aperture body 142 and a pin hole 210. Illuminator body 200 is a portion of e.g. the Universal Vertical Illuminator of a metallurgical microscope, Model BHM-313U, available from Olympus Optical Co. of Tokyo, Japan.

In the Olympus microscope, pin hole 210 is used to improve resolution in bright-field viewing especially at high magnification, e.g., 250X. For other viewing applications, e.g. darkfield viewing, pin hole 210 is removed to allow more light through illuminator body 200, and aperture body 142 is used to select an appropriate aperture diameter. Unfortunately, the Olympus system has several deficiencies. For example, because pinhole 210 must be removed to allow for use with lower magnifications, the operator must periodically go through the time-consuming process of aligning pinhole 210 along the axis of illuminator body 200. Furthermore, because aperture body 210 is centered around the focal point FP of collection lens 141, pinhole 210 is necessarily located elsewhere at a less-than-optimal location along the light path (ideally, both pinhole 210 and aperture body 142 should be centered around focal point FP). For the foregoing reasons, in accordance with the invention we have eliminated the need for pinhole 210 by increasing the range of aperture diameters over which aperture body 142 is adjusted.

Figure 3A:
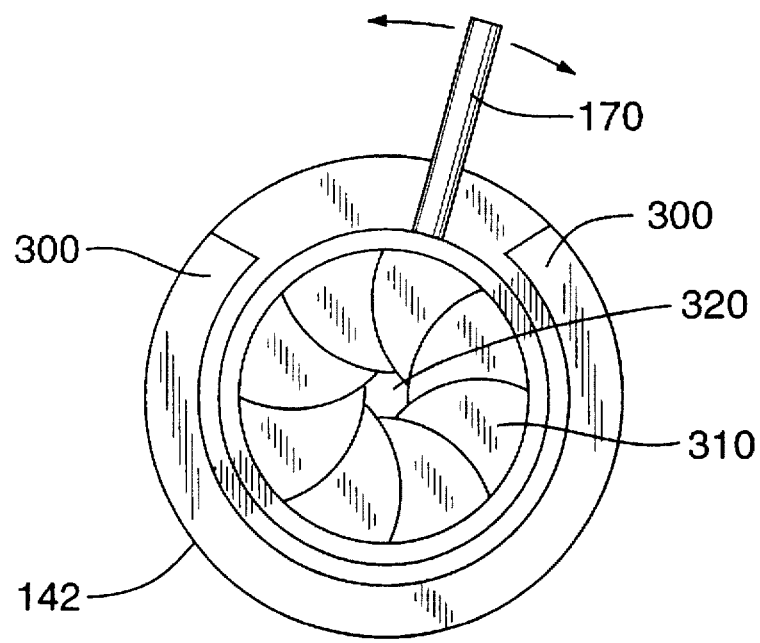
FIG. 3A is a simplified diagram showing aperture body 142 from a direction along the vertical axis of FIGS. 1 and 2.

FIG. 3A is a simplified diagram showing aperture body 142 from a direction along the vertical axis of FIGS. 1 and 2. Aperture body 142 includes aperture stop 300 and an iris 310 made up of a number of leaves. When lever 170 is moved in either direction, as specified by the arrows, iris 310 conventionally opens and closes to change the diameter of the hole defined by iris 310, aperture 320. In the embodiment of FIG. 1, the position of lever 170 is determined by stepper motor 115, which is controlled by an operator via computer 105.

Figure 3B:
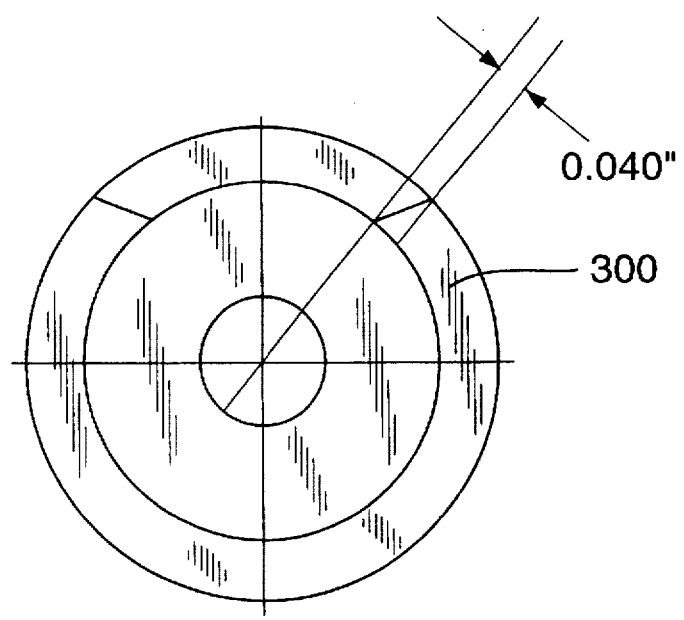
FIG. 3B is a simplified diagram of aperture stop 300 in accordance with the invention.

FIG. 3B is a simplified diagram of aperture stop 300 as modified in accordance with our invention. As is clear from FIG. 3B, forty-thousandths of an inch (0.040") of material is removed from a side surface of the structure of aperture stop 300 to allow greater movement of lever 170, and therefore a greater range of aperture diameters. Using the modification of FIG. 3B, the minimum achievable aperture diameter is changed from approximately fifty-thousandths of an inch (0.050") to approximately fifteen-thousandths of an inch (0.015"). With such a small minimum aperture, the need for a separate pin hole is eliminated, along with the associated disadvantages: the "pinhole" is now located at focal point FP, and experiments have shown that the aperture may be adjusted thousands of times without any appreciable alignment error.

According to conventional wisdom, defect detection and characterization is optimized when image resolution is as high as possible. We have found this to be generally true for relatively simple images; however, we have discovered that as the complexity of the compared image increases, so too does the probability of erroneously indicating the presence of a defect (i.e., indicating a "false positive").

After extensive experimentation, we learned that reducing image resolution actually improves defect detection and characterization for many types of targets. For this reason, we altered the resolution of the microscope by changing the diameter of aperture 320.

Although image resolution can be reduced using conventional digital image processing techniques such as smoothing, the extra processing wastes valuable time and the resulting image is inferior to those generated using a larger aperture. This is because larger apertures, while decreasing resolution, advantageously increases depth of focus. For sample targets with well-developed surface structures, the images are generally more complex in both the X-Y plane (parallel to the target surface) and the Z direction (normal to the target surface). For such complex targets, automatic defect detection (ADD) images taken with larger depth of focus and reduced resolution can provide more accurate defect detection because most defects still provide observable differences between the ADD images and calibration images, while minor image differences are obscured.

We invented a method of adjusting a microscope aperture to optimize the resolution of imaging system 100 for detecting and/or classifying defects on a given type of target. For example, in accordance with a process for fabricating conventional MOS transistors, a wafer only contains "source" and "drain" structures for the transistors. At this stage, the wafer is relatively flat and the pattern is relatively simple. Because of the simplicity of the source and drain structures, the maximum resolution (provided by the minimum aperture diameter) provides superior defect detection and classification.

As the wafer proceeds through subsequent processes additional structures (e.g., metal interconnect lines) are added to the wafer so that the wafer surface features have complex topology and complex X-Y features. Due to this complexity, a relatively low resolution image with increased depth of focus provides superior defect detection and classification.

In accordance with our invention, the visual textures of target samples are specified using a range of numbers to indicate "graininess." Higher graininess numbers indicate target types that result in relatively noisy, uneven, color varied, or complex images, while lower graininess numbers indicate target types that result in relatively simple, smooth, "clean" images. Computer 105 can then select an appropriate aperture setting for a given graininess number. For example, a target type that produces an image having high graininess may require a relatively large aperture diameter to reduce the resolution of imaging system 100 and therefore minimize the effects of the graininess. The relationship between graininess and aperture settings can be expresses as a formula; alternately, aperture diameters corresponding to particular graininess numbers can be empirically determined, as described below, and stored in a conventional lookup table.

The following series of steps, which may be used to determine the optimal aperture diameter for a particular sample type, will be understood by those familiar with the use of imaging systems similar to imaging system 100. For example, in the embodiment that includes the Ultrapointe Imaging System, the process of taking an image of a target is described in the text of the Imaging System User's Manual.

Using imaging system 100, the operator first takes an image of a calibration sample of the target material for which the operator wishes to determine the optimal imaging system resolution. As is well known to those skilled in the art, this step requires placing the calibration sample (e.g., target 140) on stage 120, focusing objective lens 155 on the calibration sample, and selecting an appropriate combination of aperture size and light-source intensity. This relatively time-consuming process is accomplished by eye to achieve a suitable image. The operator then visually analyzes the image of the calibration sample to find any defects. As described below, the image of the calibration sample with the defects (i.e., the known defect information) serves as a bench mark against which the performance of the imaging system 100 may be measured.

Once the known defect information is stored in computer 105 (e.g., as an image), the operator causes imaging system 100 to automatically take an image of the calibration sample and locate the defects. As described above, such automatic defect detection (ADD) is accomplished by comparing a sample image to an image taken from a defect-free reference surface. Defects are detected by noting the nature and extent of the differences between the two images. Imaging system 100 then produces an ADD image, which is a composite image of the calibration sample and the reference surface with the areas of difference between the two images highlighted to indicate defects.

To determine the accuracy of the last step, the ADD image is visually compared to the manually obtained image of the calibration sample. If the automatic detection step worked perfectly, the highlighted defect areas will precisely coincide with the defects observed in the manually obtained image. In other words, the visually located defect areas will have been discovered and highlighted by the ADD process. Unfortunately, such a perfect correlation is relatively rare.

The reason the correlation is usually not perfect is that the ADD process typically finds "defects" that are not defects at all, but are instead the result of e.g. misalignment of the target sample and reference sample, focus differences between the target sample and reference images, noise, and normal process variations. The accuracy of the ADD process is then defined as the ratio of true defects detected to false defects detected. If the accuracy of the ADD process is deemed to be perfect, then the parameters of imaging system 100 (e.g., aperture diameter, light intensity, and magnification) are stored in computer 105 for subsequent defect analysis of similar targets.

If, as is more likely the case, the ADD process is found to be less than perfect, the operator adjusts the resolution of imaging system 100 by changing the diameter of aperture 320 to a second diameter. The ADD process is then repeated with the new aperture diameter to obtain a second ADD image similar to the first. This second ADD image is then visually compared with the manually obtained image of the calibration sample and the accuracy of the ADD process is once again determined, this time with the altered resolution provided by the changed aperture diameter/light intensity combination. The operator then chooses the aperture diameter/light intensity combination that resulted in the most accurate defect detection. By going through the foregoing process a number of times, an operator can determine the image resolution that provides the most accurate automatic detection for the chosen target type.

The method of selecting an appropriate aperture diameter in accordance with the present invention is not limited to the particular applications described above. For example, instead of using the accuracy of the ADD process to provide feedback for selecting an appropriate aperture diameter, an operator could use defect characterization data. That is, the operator could select an aperture diameter that provides the most accurate assessment of not only the number of defects, but also the type of defect (e.g., a scratch, a pit, or a drop of photoresist). Hence, the scope of the appended claims should not be limited to the description of the embodiments described herein.

What is claimed is:

1. A method of adjusting a microscope aperture to optimize the aperture diameter for a given target type, the microscope including a defect detection system and a light source for illuminating a target, the method comprising:

providing a calibration sample of the target type, the calibration sample including one or more known defects;

providing known defect information corresponding to the known defects of the calibration sample;

obtaining a first image of the calibration sample, the step of obtaining a first image including the substeps of:
  positioning the calibration sample on a stage of the microscope,
  adjusting the aperture to a first aperture diameter, and
  adjusting the intensity of the illuminator to a first intensity;

analyzing the first image of the calibration sample, using the defect detection system, to obtain a first set of defect information;

obtaining a second image of the calibration sample, the step of obtaining a second image including the substeps of adjusting the aperture to a second aperture diameter and adjusting the intensity of the illuminator to a second intensity;

analyzing the second image of the calibration sample, using the defect detection system, to obtain a second set of defect information;

comparing the first and second sets of defect information to the known defect information to determine which one of the first and second sets of defect information best approximates the known defect information;

adjusting the microscope to the aperture diameter/ illumination intensity combination corresponding to the best set; and detecting defects on the given target type using the adjusted microscope.

2. A method of adjusting a microscope aperture to optimize the aperture diameter for a given target type, the microscope including a defect detection system and a light source for illuminating a target, the method comprising:

providing a calibration sample of the target type, the calibration sample including one or more known defects;

providing known defect information corresponding to the known defects of the calibration sample;

obtaining a first image of the calibration sample, the step of obtaining a first image including positioning the calibration sample on a stage of the microscope and adjusting the aperture to a first aperture diameter;

analyzing the first image of the calibration sample, using the defect detection system, to obtain a first set of defect information;

obtaining a second image of the calibration sample, the step of obtaining a second image including adjusting the aperture to a second aperture diameter;

analyzing the second image of the calibration sample, using the defect detection system, to obtain a second set of defect information;

comparing the first and second sets of defect information to the known defect information to determine which one of the first and second sets of defect information best approximates the known defect information;

adjusting the microscope to the aperture diameter corresponding to the best set; and detecting defects on the given target type using the adjusted microscope.

3. The method of claim 2, further comprising the steps of:

obtaining a third image of the calibration sample, the step of obtaining a third image including the substeps of adjusting the aperture to a third aperture diameter;

analyzing the third image of the calibration sample, using the defect detection system, to obtain a third set of defect information;

comparing the third set of defect information to the known defect information; and determining which one of the first, second, and third sets of defect information best approximates the known defect information.

4. The method of claim 3, further comprising the step of selecting the one of the first, second, and third aperture diameters used to obtain the one of the first second and third sets of defect information that best approximates the known defect information.

5. The method of claim 2, wherein the defect information includes the number of defects on the calibration sample.

6. The method of claim 2, wherein the defect detection system comprises means for characterizing defects, and wherein the defect information includes defect characterization data.

7. The method of claim 2, wherein the microscope further includes a controller connected to the aperture, the controller for selecting from a plurality of aperture diameters, including the first, second, and third aperture diameters.

8. The method of claim 7, wherein the controller comprises a stepper motor.

9. The method of claim 2, wherein the intensity of the illuminator is adjusted after each of the steps of adjusting the aperture.

10. A method of adjusting the resolution of a microscope to optimize the resolution for a given target type, the microscope including a defect detection system and a light source for illuminating a target, the method comprising:

provoding a calibration sample of the target type, the calibration sample including one or more known defects;

providing known defect information corresponding to the known defects of the calibration sample;

obtaining a first image of the calibration sample, the step of obtaining a first image including positioning the calibration sample on a stage of the microscope and adjusting the microscope to obtain a first resolution;

analyzing the first image of the calibration sample, using the defect detection system, to obtain a first set of defect information;

obtaining a second image of the calibration sample, the step of obtaining a second image including adjusting the microscope to obtain a second resolution;

analyzing the second image of the calibration sample, using the defect detection system, to obtain a second set of defect information;

comparing the first and second sets of defect information to the known defect information to determine which one of the first and second sets of defect information best approximates the known defect information;

adjusting the microscope to the resolution corresponding to the best set; and detecting defects on the given target type using the adjusted microscope.

11. The method of claim 10, further comprising the steps of:

obtaining a third image of the calibration sample, the step of obtaining a third image including the substeps of adjusting the microscope to obtain a third resolution;

analyzing the third image of the calibration sample, using the defect detection system, to obtain a third set of defect information;

comparing the third set of defect information to the known defect information; and determining which one of the first, second, and third sets of defect information best approximates the known defect information.

12. The method of claim 11, further comprising the step of selecting the one of the first, second, and third resolutions to obtain the one of the first second and third sets of defect information that best approximates the known defect information.

13. The method of claim 10, wherein the defect information includes the number of defects on the calibration sample.

14. The method of claim 10, wherein the defect detection system comprises means for characterizing defects, and wherein the defect information includes defect characterization data.

15. The method of claim 10, wherein the microscope further includes a controller connected to an aperture of the microscope, the controller for selecting from a plurality of aperture diameters for selecting the first, second, and third resolutions.

16. The method of claim 15, wherein the controller comprises a stepper motor.

* * * * *